United States Patent
Kobayashi et al.

(10) Patent No.: US 9,989,351 B2
(45) Date of Patent: Jun. 5, 2018

(54) TOMOGRAPHIC IMAGE CAPTURING DEVICE

(71) Applicant: KOWA COMPANY, LTD., Nagoya-shi, Aichi (JP)

(72) Inventors: Naoki Kobayashi, Higashimurayama (JP); Toshiaki Nakagawa, Higashimurayama (JP)

(73) Assignee: KOWA COMPANY, LTD. (JP)

( * ) Notice: Subject to any disclaimer, the term of this patent is extended or adjusted under 35 U.S.C. 154(b) by 0 days. days.

(21) Appl. No.: 15/329,725

(22) PCT Filed: Jul. 29, 2015

(86) PCT No.: PCT/JP2015/071443
§ 371 (c)(1),
(2) Date: Jan. 27, 2017

(87) PCT Pub. No.: WO2016/017664
PCT Pub. Date: Feb. 4, 2016

(65) Prior Publication Data
US 2017/0211925 A1    Jul. 27, 2017

(30) Foreign Application Priority Data

Jul. 30, 2014 (JP) .................................. 2014-155368

(51) Int. Cl.
*A61B 3/14* (2006.01)
*G01B 9/02* (2006.01)
(Continued)

(52) U.S. Cl.
CPC .......... *G01B 9/02091* (2013.01); *A61B 3/102* (2013.01); *A61B 3/13* (2013.01);
(Continued)

(58) Field of Classification Search
CPC .... A61B 3/02; A61B 3/13; A61B 3/15; G01B 9/02091; G01B 9/02068; G01B 9/02027;
(Continued)

(56) References Cited

U.S. PATENT DOCUMENTS

2010/0110375 A1  5/2010  Nishio et al. ................. 351/206
2012/0044457 A1  2/2012  Sato et al. .................... 351/206

FOREIGN PATENT DOCUMENTS

EP     3165151      5/2017
JP     2008267891   11/2008

OTHER PUBLICATIONS

International Search Report dated Nov. 2, 2015, issued in International Application No. PCT/JP2015/071443 together with English-language translation thereof.
(Continued)

*Primary Examiner* — Jack Dinh
(74) *Attorney, Agent, or Firm* — Adams & Wilks (57) ABSTRACT

The tomographic image capturing device of the present invention comprises a display means (18) configured to: split light from a light source (11) into measurement light and reference light and cause the measurement light and the reference light to be incident to an object (E) and a reference object (49), respectively; capture tomographic images of the object (E) on the basis of interference light generated by superposition of the measurement light reflected from the object (E) and the reference light reflected from the reference object (49); and display tomographic pictures of the object generated on the basis of the captured tomographic images. The tomographic image capturing device has a first image capturing mode and a second image capturing mode. The first image capturing mode is a mode in which the measurement light is two-dimensionally scanned by raster scan to be incident to the object (E) and the tomographic images of the object (E) are captured. The second image capturing mode is a mode in which the measurement light is two-dimensionally scanned by raster scan to be incident to the object (E) and the tomographic images of the object (E) are captured. The raster scan in the second image capturing mode is thinned from the raster scan in the first image capturing mode. The display means (18) is configured to be switchable between a first display mode and a second display mode. The first display mode is a mode in which a plurality of tomographic pictures including a region of interest of the object (E) is selected from among the tomographic pictures generated on the basis of the tomographic images captured in the second image capturing mode and
(Continued)

only the selected plurality of tomographic pictures is displayed. The second display mode is a mode in which all of the tomographic pictures generated on the basis of the tomographic images captured in the second image capturing mode are in turn displayed. The capturing of the tomographic images in the first image capturing mode is performed after separately performing a first adjustment operation and a second adjustment operation for adjustment of an image capturing condition necessary for capturing the tomographic images in the first image capturing mode. The first adjustment operation is based on the tomographic pictures displayed in the first display mode. The second adjustment operation is based on the tomographic pictures displayed in the second display mode.

5 Claims, 6 Drawing Sheets (51) Int. Cl.
*A61B 3/10* (2006.01)
*A61B 3/13* (2006.01)
*A61B 3/15* (2006.01)
*G01B 11/02* (2006.01)

(52) U.S. Cl.
CPC .............. *A61B 3/15* (2013.01); *G01B 9/0203* (2013.01); *G01B 9/02027* (2013.01); *G01B 9/02068* (2013.01); *G01B 9/02077* (2013.01); *G01B 11/02* (2013.01)

(58) Field of Classification Search
CPC ... G01B 9/0203; G01B 9/02077; G01B 11/02
USPC .......................................................... 351/208
See application file for complete search history.

(56) References Cited

OTHER PUBLICATIONS

European Search Report dated Feb. 22, 2018 issued in Application No. 15827667.5.

<Preliminary image capturing mode>
(Selective display mode)

(a)

<Preliminary image capturing mode>
(Sequential display mode)

(b)

<Main image capturing mode>

(a) <Preliminary image capturing mode>
(Selective display mode)

(b) <Preliminary image capturing mode>
(Sequential display mode)

(c) <Main image capturing mode>

(When tomographic images are captured)

(When alignment operation is performed)

TOMOGRAPHIC IMAGE CAPTURING DEVICE

TECHNICAL FIELD

The present invention relates to a tomographic image capturing device that captures a tomographic image of an object such as a subject's eye on the basis of interference light generated by superposition of measurement light from the object and reference light.

BACKGROUND ART

As a type of ophthalmic diagnostic equipment, there are tomographic image capturing devices that utilize optical interference of so-called OCT (Optical Coherence Tomography) to capture tomographic images of ocular fundi. Such tomographic image capturing devices can capture tomographic images of ocular fundi at high sensitivity through irradiating the ocular fundi with broadband and low coherent light and causing the reflected light from the ocular fundi to interfere with reference light. When the horizontal direction, vertical direction and depth of an ocular fundus are represented by x-direction, y-direction and z-direction, respectively, such a tomographic image capturing device can acquire tomographic pictures (B-scan pictures) in the xz-directions. In ordinary image capturing of OCT, the tomographic images are captured, for example, at a rate of 40 images per second and a set of 100 or more tomographic pictures of a retina can be acquired by one-time testing (image capturing at a part of the retina).

Figure 7:
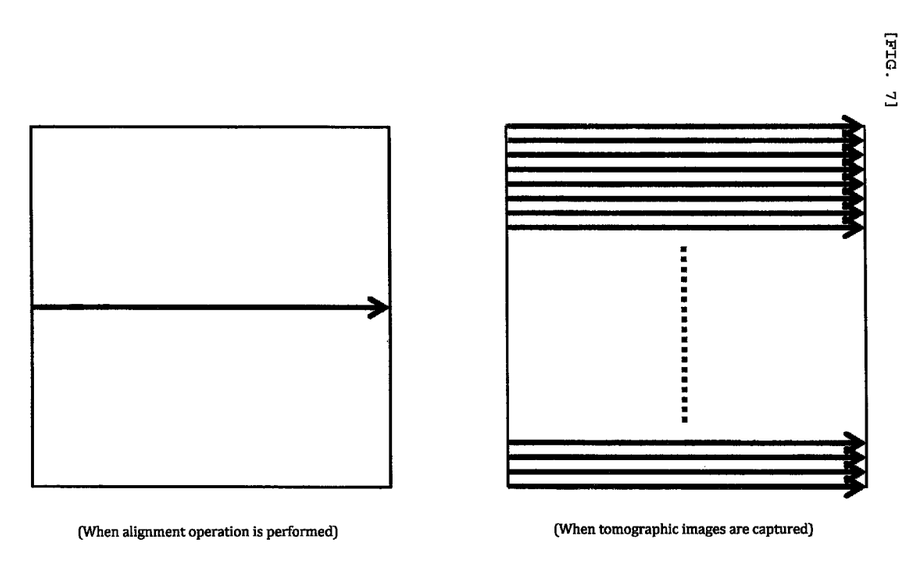
FIG. 7 is an explanatory view illustrating scanning patterns at the time of adjusting the image capturing condition and at the time of image capturing in a conventional tomographic image capturing device.

In general, when capturing tomographic images, adjustment of an image capturing condition, such as positioning of an image capturing site and reference mirror, focus adjustment, and determination of a dispersion compensation glass, may be performed before the image capturing so that optimum tomographic pictures of an ocular fundus are obtained. As illustrated in FIG. 7, when raster scan is performed for image capturing of a three-dimensional tomographic structure, there is a method in which adjustment of the image capturing condition before the image capturing is performed while observing tomographic pictures obtained by sequentially scanning only in a high-speed axis direction (x-direction) at the center of a scanning field angle that is two-dimensionally set, and thereafter the original scanning field angle as a whole is raster-scanned at the time of actually capturing tomographic images. In such a method, the tomographic pictures obtained at the time of adjustment of the image capturing condition are approximately fixed and the form variation of the image capturing site is less likely to occur in the tomographic pictures. Therefore, adjustment can easily be performed for the appearance position of the image capturing site in the tomographic pictures and for the image capturing condition, such as focus adjustment, which may be advantageous.

On the other hand, when the raster scan area is wide, when the object is an eye of high myopia, when images of the peripheral area of a retina are captured, when images of an area of optic papilla are captured, or in similar cases, the curvature of captured tomographic pictures is large, so that the appearance positions of the image capturing site in the tomographic pictures differ in accordance with the scanning position. Therefore, an appropriate focus position and reference mirror position cannot be determined even if the image capturing condition is optimized by performing adjustment of the image capturing condition on the basis of the tomographic pictures obtained only by scanning the center position of raster scan because the form of the measurement object cannot be perceived except the center position of raster scan. As a result, in the tomographic pictures obtained by scanning other parts than the center position of raster scan, defocus and/or replication of the tomographic structure of the image capturing site may possibly occur. In addition, if the appearance position of image capturing site is unnecessarily set below to prevent such replication, the image contrast may deteriorate.

SUMMARY OF THE INVENTION

Problems to be Solved by the Invention

If, also at the time of adjusting the image capturing condition, the raster scan area as a whole is scanned as in the image capturing of tomographic images, all of the tomographic pictures of the image capturing site can be observed during the adjustment of the image capturing condition and an optimum image capturing condition can thus be determined. This is said to be ideal. However, the raster scan of the scanning area as a whole takes time and the adjustment of image capturing condition requires a long period of time. Actual image capturing of the tomographic images is after performing adjustment of the image capturing condition to optimize the image capturing condition, and the sequence of image capturing operations takes time, which may restrain the subject from moving until the image capturing is completed. Therefore, the image capturing operations may readily be affected by the disturbance such as involuntary eye movements. If large involuntary eye movements occur, adjustment of the image capturing condition will be necessary again. This may lead to a negative spiral that the image capturing requires a longer period of time.

The present invention has been made in consideration of the above and an object of the present invention is to provide a tomographic image capturing device that can complete adjustment of the image capturing condition in a short time to determine an optimum image capturing condition.

Means for Solving the Problems

To solve the above object, the present invention provides a tomographic image capturing device comprising a display means configured to: split light from a light source into measurement light and reference light and cause the measurement light and the reference light to be incident to an object and a reference object, respectively; capture tomographic images of the object on the basis of interference light generated by superposition of the measurement light reflected from the object and the reference light reflected from the reference object; and display tomographic pictures of the object generated on the basis of the captured tomographic images, the tomographic image capturing device having a first image capturing mode and a second image capturing mode, the first image capturing mode being a mode in which the measurement light is two-dimensionally scanned by raster scan to be incident to the object and the tomographic images of the object are captured, the second image capturing mode being a mode in which the measurement light is two-dimensionally scanned by raster scan to be incident to the object and the tomographic images of the object are captured, the raster scan in the second image capturing mode being thinned from the raster scan in the first image capturing mode, the display means being configured to be switchable between a first display mode and a second display mode, the first display mode being a mode in which a plurality of tomographic pictures including a region of interest of the object is selected from among the tomographic pictures generated on the basis of the tomographic images captured in the second image capturing mode and only the selected plurality of tomographic pictures is displayed, the second display mode being a mode in which all of the tomographic pictures generated on the basis of the tomographic images captured in the second image capturing mode are in turn displayed, the capturing of the tomographic images in the first image capturing mode being performed after separately performing a first adjustment operation and a second adjustment operation for adjustment of an image capturing condition necessary for capturing the tomographic images in the first image capturing mode, the first adjustment operation being based on the tomographic pictures displayed in the first display mode, the second adjustment operation being based on the tomographic pictures displayed in the second display mode (Invention 1). The "region of interest" as used herein refers to a region that represents a change in form of the image capturing object within a scanning region in the first image capturing mode.

In the present application, examples of adjustment of the image capturing condition necessary for capturing tomographic images in the first image capturing mode include various adjustment operations that are performed before image capturing of the tomographic images to obtain optimum tomographic pictures of an ocular fundus, such as alignment of the tomographic image capturing device and a subject's eye as the object, focus adjustment to move the position of a focusing lens for focusing in accordance with the diopter scale of a subject's eye, reference mirror positioning to move the position of a reference mirror to match the optical path lengths of the measurement optical system and reference optical system so that interference light is generated by superposition of the measurement light and reference light, and dispersion compensation glass determination to select an appropriate dispersion compensation glass for compensating for refractive index dispersion that causes blurred tomographic images.

In the present application, the first adjustment operation means performing dispersion compensation glass determination to select an appropriate dispersion compensation glass in order to compensate for refractive index dispersion that causes blurred tomographic images and performing focus adjustment to move the position of a focusing lens for focusing in accordance with the diopter scale of a subject's eye. In the present application, the second adjustment operation means performing focus adjustment to move the position of a focusing lens for focusing in accordance with the diopter scale of a subject's eye and performing reference mirror positioning to move the position of a reference mirror to match the optical path lengths of the measurement optical system and reference optical system so that interference light is generated by superposition of the measurement light and reference light.

First, according to the above invention (Invention 1), the second image capturing mode is provided to capture tomographic images by the thinned raster scan which requires a shorter time than that in the first image capturing mode and therefore the adjustment of image capturing condition can be completed in a short time by performing, in the second image capturing mode, the adjustment of image capturing condition necessary for capturing tomographic images in the first image capturing mode. Moreover, an optimum image capturing condition can be determined because the image capturing of tomographic images in the second image capturing mode is two-dimensionally performed by the raster scan which is thinned from the raster scan in the first image capturing mode, rather than by one-dimensional scanning at the center position or the like of raster scan as in the prior art, and tomographic pictures that almost entirely cover the image capturing site can thereby be observed during the adjustment of image capturing condition. Furthermore, the first adjustment operation, in which the adjustment can be appropriately performed on the basis only of specific tomographic pictures, and the second adjustment operation, in which the adjustment can be more appropriately performed rather on the basis of the plurality of tomographic pictures obtained by scans that almost entirely cover the image capturing site, can be separately performed, and a more appropriate image capturing condition can thereby be determined in a short time. During this operation, the first adjustment operation may be technically possible based only on one specific tomographic picture, but in this case, even though the first adjustment operation can be appropriately performed at the site where the one specific tomographic picture is acquired, optimum adjustment may not be performed at other sites. In this regard, a plurality of tomographic pictures including a region of interest of the object may be selected for the first adjustment operation thereby to appropriately perform the first adjustment operation at a plurality of sites. This operation allows the adjustment of image capturing condition to be more accurately carried out.

In the above invention (Invention 1), in the first display mode, the display means may display the selected plurality of tomographic pictures repetitively in turn (Invention 2) or may display the selected plurality of tomographic pictures side by side in the same screen (Invention 3).

In the above invention (Invention 2, 3), only a desired selected region may be able to be displayed for each of the selected plurality of tomographic pictures (Invention 4). The "desired selected region" as used herein refers to a partial region of tomographic picture that is selected so as to include a tomographic structure of the object to such an extent that is necessary for performing the first adjustment operation.

In the above invention (Invention 3), only a region including a tomographic structure of the object may be enlarged for each of the selected plurality of tomographic pictures and the enlarged tomographic pictures may be displayed side by side in the same screen (Invention 5).

When the selected plurality of tomographic pictures is displayed side by side in the same screen, the picture size of one tomographic picture to be displayed decreases as the number of the tomographic pictures increases and observation of details may be difficult. According to the above invention (Invention 5), a part of tomographic picture that does not include the tomographic structure of the object is essentially unnecessary for the first adjustment operation and therefore excluded from the displaying object, and only a region that includes the tomographic structure of the object necessary for the first adjustment operation may be enlarged thereby to allow for observation of details of the tomographic structure in each picture even when the plurality of tomographic pictures is displayed side by side in the same screen.

Advantageous Effect of the Invention

According to the tomographic image capturing device of the present invention, adjustment of the image capturing condition can be completed in a short time to determine an optimum image capturing condition.

EMBODIMENTS FOR CARRYING OUT THE INVENTION

First Embodiment

Hereinafter, a first embodiment of the present invention will be described in detail with reference to the drawings.

Figure 1:
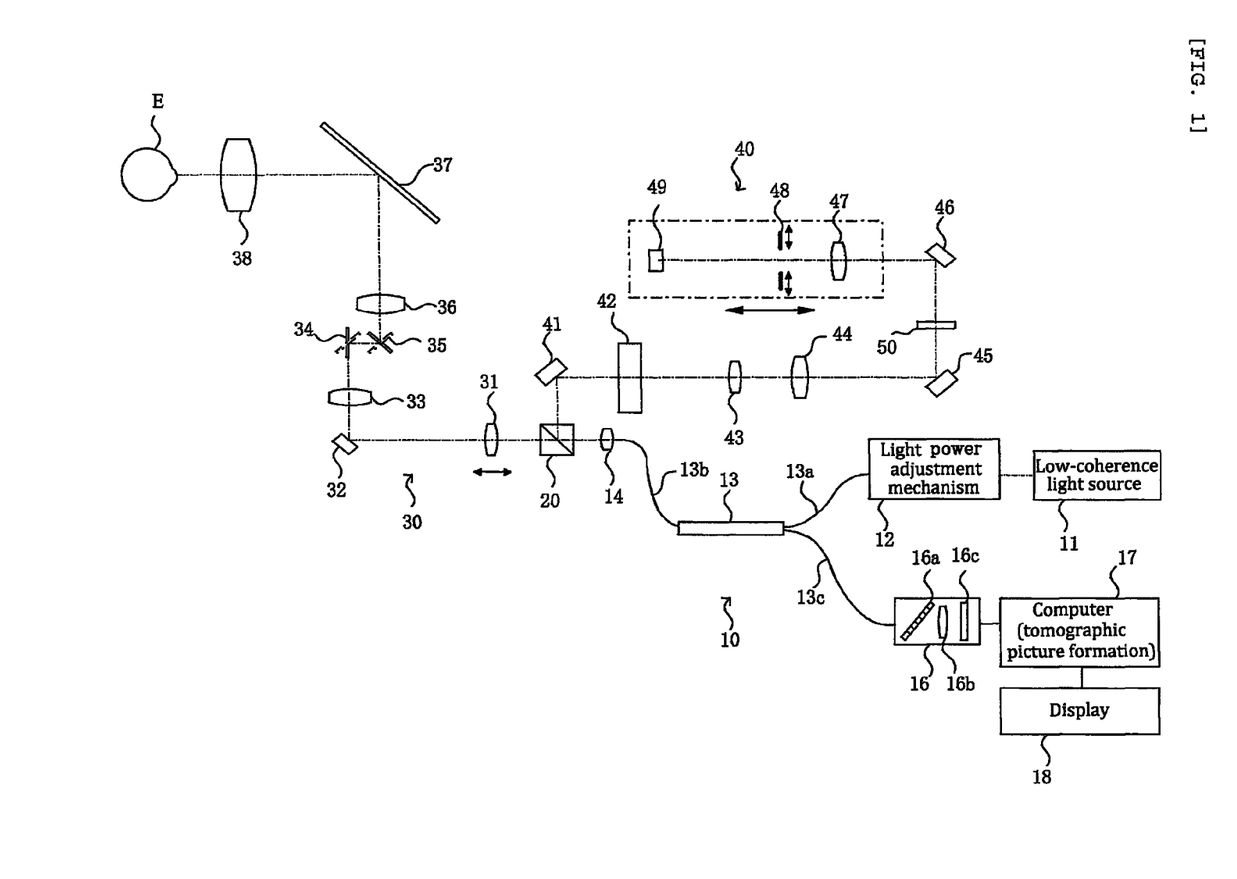
FIG. 1 is an optics view illustrating the overall configuration of a tomographic image capturing device according to a first embodiment of the present invention.

FIG. 1 is an optics view illustrating the overall configuration of a tomographic image capturing device according to the first embodiment of the present invention. The tomographic image capturing device according to the present embodiment, which can be applied to an ocular fundus of a subject's eye E as the image capturing object, is to capture tomographic images of a desired region of the ocular fundus by raster scan. The part denoted by reference numeral 10 is a demultiplexing/multiplexing optical system. This optical system may be provided with a broadband low-coherence light source 11 that comprises, for example, a super-luminescent diode (SLD) and emits light of a temporal coherence length of about several micrometers to several tens of micrometers at a wavelength of 700 nm to 1,100 nm.

The low-coherence light generated from the low-coherence light source 11 passes through a light power adjustment mechanism 12, in which the light power is adjusted, and is incident to an optical coupler 13 via an optical fiber 13a and then introduced into a beam splitter 20 as a splitting optical element via an optical fiber 13b and collimator lens 14. Demultiplexing and/or multiplexing may also be performed using an optical circulator as substitute for the optical coupler 13.

The light incident to the beam splitter 20 is split into reference light and measurement light. The measurement light is incident to a focusing lens 31, which is to focus the measurement light on the ocular fundus of the subject's eye E. The measurement light to be focused on the ocular fundus is reflected by a mirror 32, passes through a lens 33, and is scanned in an arbitrary direction by an x-axis scanning mirror (galvanometer mirror) 34 and y-axis scanning mirror (galvanometer mirror) 35. The measurement light scanned by the x-axis and y-axis scanning mirrors 34 and 35 passes through a scanning lens 36, is reflected by a dichroic mirror 37, and then passes through an objective lens 38 to be incident to the ocular fundus, which is thus scanned by the measurement light in the x-direction and y-direction. The measurement light reflected by the ocular fundus tracks back the above path to return to the beam splitter 20.

In such an optical system, the focusing lens 31, mirror 32, lens 33, x-axis scanning mirror 34, y-axis scanning mirror 35, scanning lens 36, dichroic mirror 37 and objective lens 38, which are located downstream the beam splitter 20, may constitute a measurement optical system 30 of the tomographic image capturing device.

On the other hand, the reference light split by the beam splitter 20 is reflected by a mirror 41 and then passes through a dispersion compensation glass for objective lens 42 and lenses 43 and 44. Thereafter, the reference light is reflected by a mirror 45 and passes through a subject's eye dispersion compensation glass 50 that compensates for the refractive index dispersion of the subject's eye E as the object. Then, the reference light is reflected by a dichroic mirror 46, passes through a focusing lens 47 and variable aperture 48, and reaches a reference mirror 49. The variable aperture 48 may adjust the light power. To adjust the optical path length, the focusing lens 47, variable aperture 48 and reference mirror 49 can move in the optical axis direction in an integrated manner, as indicated by the double-headed arrow in FIG. 1. The reference light reflected by the reference mirror 49 tracks back the above path to return to the beam splitter 20.

In the present embodiment, the focusing lens 31, lens 33, scanning lens 36 and objective lens 38 of the measurement optical system 30 may correspond respectively to the lens 43, lens 44, focusing lens 47 and dispersion compensation glass for objective lens 42 of the reference optical system 40, and respective dispersion characteristics may be the same or equivalent. The mirror 32, x-axis scanning mirror 34, y-axis scanning mirror 35 and dichroic mirror 37 of the measurement optical system 30 may correspond respectively to the mirror 41, mirror 45, reference mirror 49 and dichroic mirror 46 of the reference optical system 40, and respective dispersion characteristics may also be the same or equivalent. The dispersion characteristics of the subject's eye E and the dispersion characteristics of the subject's eye dispersion compensation glass 50 may also be the same or equivalent.

In such an optical system, the mirror 41, dispersion compensation glass for objective lens 42, lenses 43 and 44, mirror 45, subject's eye dispersion compensation glass 50, dichroic mirror 46, focusing lens 47 and reference mirror 49 may constitute a reference optical system 40 of the tomographic image capturing device. The reference mirror 49 may act as a reference object.

The measurement light and reference light returned to the beam splitter 20 are superposed with each other to be interference light, which passes through the collimator lens 14 and optical coupler 13 and is incident to a spectroscope 16 via an optical fiber 13c. The spectroscope 16 may have a diffraction grating 16a, imaging lens 16b, line sensor 16c, and other necessary components. The interference light is diffracted by the diffraction grating 16a into a spectrum in accordance with the wavelength of the low-coherence light and forms an image on the line sensor 16c by the imaging lens 16b.

Signals from the line sensor 16c may be subjected to signal processing, including Fourier transformation, performed by a tomographic picture forming means that is realized using one or more CPUs of a computer 17 and the like. This signal processing generates a depth signal that represents information in the depth direction (z-direction) of the ocular fundus. When scanning the ocular fundus, the interference light at each sampling time point allows the depth signal (A-scan picture) at the sampling time point to be obtained. Therefore, completion of one scanning can form a two-dimensional tomographic picture (B-scan picture) that comprises a z-direction picture (A-scan picture) along the scanning direction. The formed tomographic picture (B-scan picture) can be displayed on the display 18. The formed tomographic picture can also be stored in a storage part (not illustrated) of the computer 17.

The tomographic image capturing device according to the present embodiment may perform some adjustments of the image capturing condition to optimize the image capturing condition when actually capturing tomographic images. Examples of adjustments of the image capturing condition include, for example, alignment of the tomographic image capturing device and the subject's eye E as the object, focus adjustment to move the position of the focusing lens 31 for focusing in accordance with the diopter scale of the subject's eye E, reference mirror positioning to move the position of the reference mirror 49 to match the optical path lengths of the measurement optical system and reference optical system so that interference light is generated by superposition of the measurement light and reference light, and dispersion compensation glass determination to select an appropriate dispersion compensation glass 50 for compensating for refractive index dispersion that causes blurred tomographic images.

The tomographic image capturing device according to the present embodiment may be configured to be switchable between a preliminary image capturing mode (second image capturing mode) and a main image capturing mode (first image capturing mode). In the preliminary image capturing mode, tomographic images for adjusting the image capturing condition are captured. In the main image capturing mode, tomographic images for actually obtaining tomographic pictures of a desired region (scanning region) of the ocular fundus are obtained after an optimum image capturing condition is determined by the adjustment of image capturing condition. Specifically, the tomographic image capturing device may capture tomographic images using different scanning patterns in the preliminary image capturing mode and main image capturing mode and can switch between the preliminary image capturing mode and the main image capturing mode by an image capturing mode switching operation.

Figure 2:
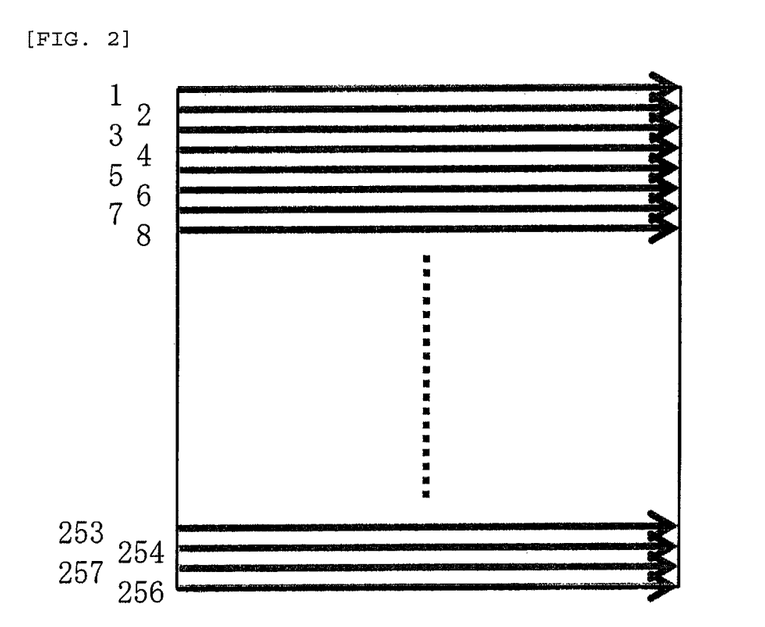
FIG. 2 is an explanatory view illustrating a scanning pattern in a main image capturing mode of the first embodiment.

In the main image capturing mode, as illustrated in FIG. 2, the scanning region as a whole may be raster-scanned. In the main image capturing mode of the present embodiment, scanning may be performed 256 times in total in the high-speed axis direction (x-direction), but is not limited thereto and may be appropriately modified in accordance with the image capturing object, purpose of image capturing, and/or size of the scanning region.

Figure 3:
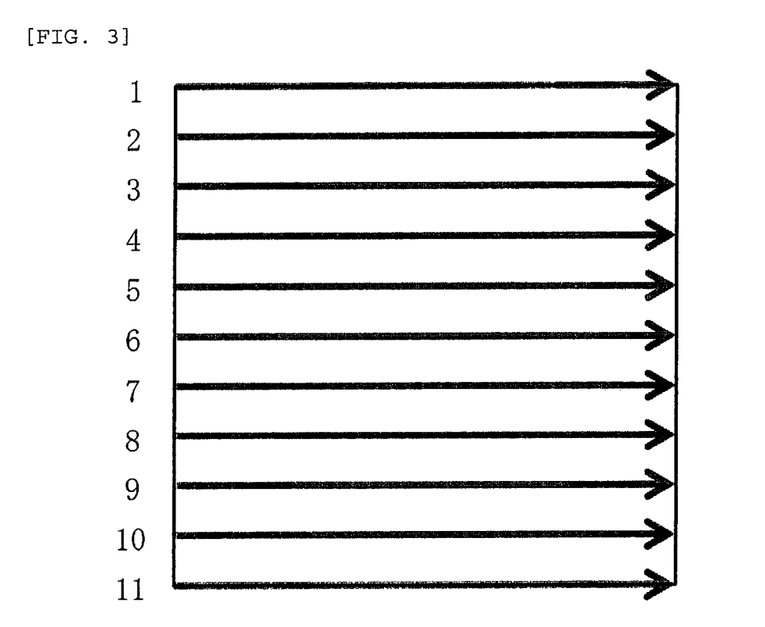
FIG. 3 is an explanatory view illustrating a scanning pattern in a preliminary image capturing mode of the first embodiment.

In the preliminary image capturing mode, as illustrated in FIG. 3, the scanning interval in the low-speed axis direction (y-direction) may be enlarged thereby to perform scanning of a more coarse scanning density than that in the main image capturing mode, that is, thinned scanning from the scanning in the high-speed axis direction (x-direction) of the raster scan in the main image capturing mode. In the preliminary image capturing mode of the present embodiment, scanning may be performed 11 times in total in the high-speed axis direction (x-direction), but is not limited thereto and may be appropriately modified in accordance with the image capturing object, purpose of image capturing, and/or size of the scanning region. Optimization of the image capturing condition can be appropriately carried out when the number of scans is sufficient for perceiving a change in shape of the object at least in the scanning region. However, the number of scans in the preliminary image capturing mode may preferably be set within a range of ½ to 1/20 of the number of scans in the main image capturing mode because the preliminary image capturing mode is expected to have an effect of reducing the time required for capturing the tomographic images for adjustment of the image capturing condition by making the scanning density more coarse than that in the main image capturing mode, that is, an effect of completing the adjustment of image capturing condition in a short time.

In the present embodiment, the scanning region in the preliminary image capturing mode may be a region that is the same as the scanning region in the main image capturing mode. Therefore, the region of interest within the scanning region in the main image capturing mode is included in the scanning region in the preliminary image capturing mode, as will be understood. Here, the region of interest refers to a region that represents a change inform of the image capturing object (ocular fundus of the subject's eye) within the scanning region in the main image capturing mode.

In the present embodiment, when displaying the tomographic pictures of the ocular fundus of the subject's eye E which are generated from the tomographic images captured in the preliminary image capturing mode, two display modes of a selective display mode and a sequential display mode may be prepared. These display modes can be switched using a display mode switching button (not illustrated).

The selective display mode refers to a display scheme in which a plurality of tomographic pictures including the region of interest of the object is selected from among the tomographic pictures generated on the basis of the tomographic images captured in the preliminary image capturing mode and only the selected plurality of tomographic pictures is displayed on the display 18. In the present embodiment, only three tomographic pictures generated on the basis of the tomographic images captured through scans at both end positions in y-direction and the center position within the scanning region (scans of No. 1, No. 6 and No. 11 in FIG. 3) may be displayed repetitively in turn.

The sequential display mode refers to a display scheme in which the tomographic pictures generated on the basis of the tomographic images captured in the preliminary image capturing mode are in turn sequentially displayed. In the present embodiment, 11 tomographic pictures generated on the basis of the tomographic images captured through all the scans (scans of No. 1 to No. 11 in FIG. 3) may be displayed repetitively in turn.

In the present embodiment, the adjustment of image capturing condition may be divided into two stages of a first adjustment operation and a second adjustment operation, and the previously-described selective display mode may be used to perform the first adjustment operation while the sequential display mode may be used to perform the second adjustment operation. The first adjustment operation may include performing dispersion compensation glass determination to select an appropriate dispersion compensation glass 50 in order to compensate for refractive index dispersion that causes blurred tomographic images and performing focus adjustment to move the position of the focusing lens 31 for focusing in accordance with the diopter scale of the subject's eye E. The second adjustment operation may include performing focus adjustment to move the position of the focusing lens 31 for focusing in accordance with the diopter scale of the subject's eye E and performing reference mirror positioning to move the position of the reference mirror 49 to match the optical path lengths of the measurement optical system and reference optical system so that interference light is generated by superposition of the measurement light and reference light.

Thus, the first adjustment operation, in which the adjustment can be appropriately performed on the basis only of specific tomographic pictures, and the second adjustment operation, in which the adjustment can be more appropriately performed rather on the basis of the plurality of tomographic pictures obtained by scans that almost entirely cover the image capturing site, can be separately performed, and a more appropriate image capturing condition can thereby be determined in a short time. During this operation, the first adjustment operation may be technically possible based only on one specific tomographic picture, but in this case, even though the first adjustment operation can be appropriately performed at the site where the one specific tomographic picture is acquired, optimum adjustment may not be performed at other sites. In this regard, a plurality of tomographic pictures (three tomographic pictures in the present embodiment) including the region of interest of the object may be selected for the first adjustment operation thereby to appropriately perform the first adjustment operation at a plurality of sites. This operation allows the adjustment of image capturing condition to be more accurately carried out.

Figure 4:
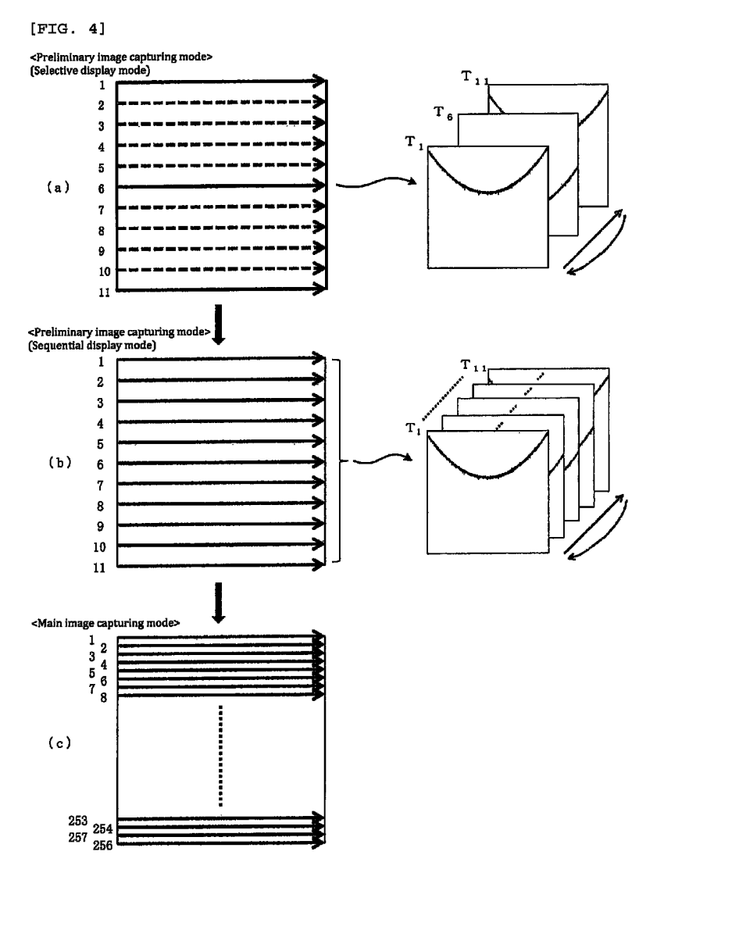
FIG. 4 is an explanatory view illustrating a flow of switching from the preliminary image capturing mode to the main image capturing mode in the first embodiment.

Description will now be directed to a flow of the adjustment of image capturing condition using switching between the preliminary image capturing mode and the main image capturing mode and switching between the selective display mode and the sequential display mode in the present embodiment. As illustrated in FIG. 4(a), first, the first adjustment operation may be performed in the preliminary image capturing mode, but the first adjustment operation is capable of appropriate adjustment based only on specific tomographic pictures. In this operation, therefore, the display 18 may be set in the selective display mode and display three tomographic pictures repetitively in turn. These three tomographic pictures may be a tomographic picture $T_1$ that is generated on the basis of a tomographic image captured by the scan of No. 1, a tomographic picture $T_6$ that is generated on the basis of a tomographic image captured by the scan of No. 6, and a tomographic picture $T_{11}$ that is generated on the basis of a tomographic image captured by the scan of No. 11.

After completion of the first adjustment operation in the selective display mode, the image capturing scheme may remain in the preliminary image capturing mode while the display mode switching button may be pressed to switch the display 18 to the sequential display mode to perform the second adjustment operation in which, as illustrated in FIG. 4(b), the adjustment can be more appropriately performed rather on the basis of the plurality of tomographic pictures obtained by scans that almost entirely cover the image capturing site. In the sequential display mode, all of the tomographic images $T_1$ to $T_{11}$ obtained in the preliminary image capturing mode may be displayed repetitively in turn.

After completion of the second adjustment operation in the sequential display mode, the display mode switching button may be pressed to switch from the preliminary image capturing mode to the main image capturing mode in which, as illustrated in FIG. 4(c), 256 raster scans in total may be performed in the high-speed axis direction (x-direction) within the entire scanning region to capture tomographic images of the ocular fundus of the subject's eye E under the optimized image capturing condition.

As will be understood, the selective display mode and the sequential display mode are merely different in the display scheme for the tomographic pictures. Regardless of whether the selective display mode or the sequential display mode is selected, the image capturing itself of tomographic images of the subject's eye E may be performed through 11 scans in total of No. 1 to No. 11 under the preliminary image capturing mode. In other words, even when the selective display mode is set, scans of No. 1 to No. 11 may be performed to capture the tomographic images necessary for generating the tomographic pictures $T_1$ to $T_{11}$, rather than performing only the scan of No. 6 to capture only the tomographic image for generating the tomographic picture $T_6$.

Data of tomographic images captured in the preliminary image capturing mode and tomographic pictures generated based thereon may be stored in a storage part (not illustrated) of the computer 17. The tomographic pictures acquired by image capturing in the preliminary image capturing mode are those obtained through raster scan at a speed of several times to several tens of times higher than that for the tomographic pictures obtained by image capturing in the main image capturing mode. Therefore, image capturing is possible while suppressing the position shift due to involuntary eye movements in the low-speed axis direction. Each tomographic picture acquired in the preliminary image capturing mode can be used as the basis to perform correction of the position shift for relocation of the tomographic pictures acquired in the main image capturing mode and it is thus possible to obtain high-density pictures from which the influence of involuntary eye movements is eliminated.

As described above, according to the tomographic image capturing device of the present embodiment, the preliminary image capturing mode is provided to capture tomographic images by the thinned raster scan which requires a shorter time than that in the main image capturing mode, and the time required for the two-dimensional scan in the preliminary image capturing mode can be shorter than that for the two-dimensional scan in the main image capturing mode. Therefore, the adjustment of image capturing condition can be completed in a short time by performing, in the preliminary image capturing mode, the adjustment of image capturing condition necessary for capturing tomographic images in the main image capturing mode. Moreover, an optimum image capturing condition can be determined because the image capturing of tomographic images in the preliminary image capturing mode is two-dimensionally performed by the raster scan which is thinned from the raster scan in the main image capturing mode and thus has a coarse scanning density, rather than by one-dimensional scanning at the center position or the like of raster scan as in the prior art, and tomographic pictures that almost entirely cover the image capturing site can thereby be observed during the adjustment of image capturing condition. Furthermore, the first adjustment operation, in which the adjustment can be appropriately performed on the basis only of specific tomographic pictures, and the second adjustment operation, in which the adjustment can be more appropriately performed rather on the basis of the plurality of tomographic pictures obtained by scans that almost entirely cover the image capturing site, can be separately performed, and a more appropriate image capturing condition can thereby be determined in a short time. During this operation, the first adjustment operation may be technically possible based only on one specific tomographic picture, but in this case, even though the first adjustment operation can be appropriately performed at the site where the one specific tomographic picture is acquired, optimum adjustment may not be performed at other sites. In this regard, a plurality of tomographic pictures including a region of interest of the object may be selected for the first adjustment operation thereby to appropriately perform the first adjustment operation at a plurality of sites. This operation allows the adjustment of image capturing condition to be more accurately carried out.

Second Embodiment

Next, a second embodiment of the present invention will be described in detail with reference to the drawings. The overall configuration of the tomographic image capturing device according to the second embodiment is identical to that of the tomographic image capturing device according to the first embodiment and the description of the optical systems and others will be omitted. The same or similar elements, components and devices as in the first embodiment are denoted by the same reference numerals and the same term is used as having the same meaning.

As in the tomographic image capturing device according to the first embodiment, the tomographic image capturing device according to the present embodiment may be prepared with two display modes of a selective display mode and a sequential display mode when displaying the tomographic pictures of the ocular fundus of the subject's eye which are generated from the tomographic images captured in the preliminary image capturing mode. These display modes can be switched using a display mode switching button (not illustrated). The configuration of the selective display mode is different from that of the first embodiment and only this aspect will be described below.

The selective display mode of the tomographic image capturing device according to the present embodiment refers to a display scheme in which a plurality of tomographic pictures including the region of interest of the object is selected from among the tomographic pictures generated on the basis of the tomographic images captured in the preliminary image capturing mode and only the selected plurality of tomographic pictures is displayed on the display 18. In the present embodiment, three tomographic pictures generated on the basis of the tomographic images captured through scans at both end positions in y-direction and the center position within the scanning region (scans of No. 1, No. 6 and No. 11 in FIG. 3) may be concurrently displayed side by side in the same screen.

Figure 5:
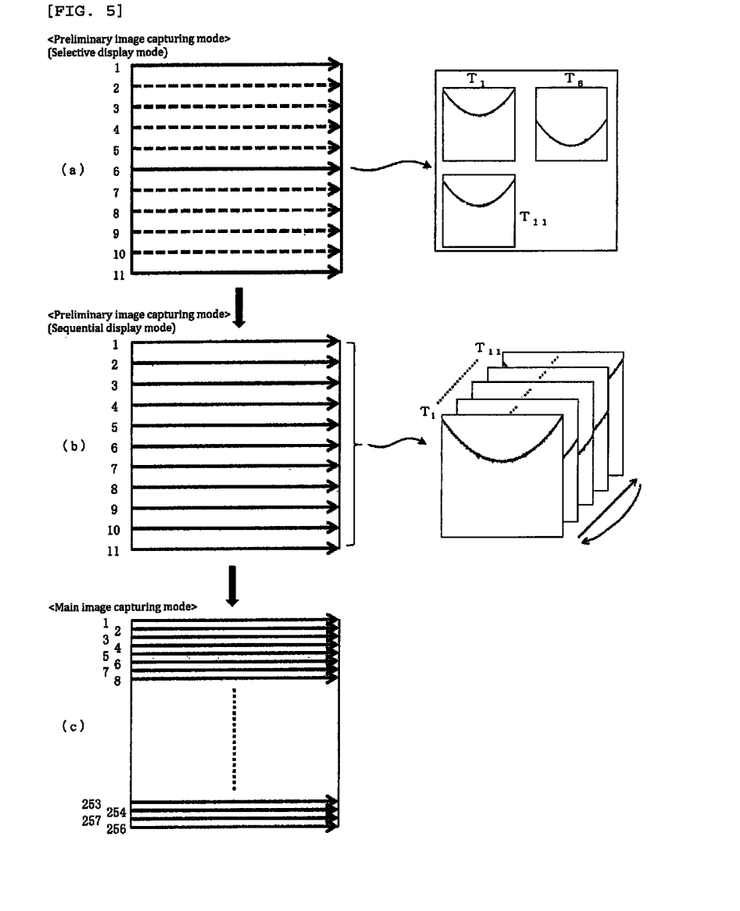
FIG. 5 is an explanatory view illustrating a flow of switching from the preliminary image capturing mode to the main image capturing mode in a second embodiment of the present invention.

In the present embodiment, as illustrated in FIG. 5(*a*), three tomographic pictures may be displayed side by side in the same screen. These three tomographic pictures may be a tomographic picture $T_1$ that is generated on the basis of a tomographic image captured by the scan of No. 1, a tomographic picture $T_6$ that is generated on the basis of a tomographic image captured by the scan of No. 6, and a tomographic picture $T_{11}$ that is generated on the basis of a tomographic image captured by the scan of No. 11. The first adjustment operation may be performed on the basis of the display on the display 18.

After completion of the first adjustment operation in the selective display mode, the image capturing scheme may remain in the preliminary image capturing mode while the display mode switching button may be pressed to switch the display 18 to the sequential display mode to perform the second adjustment operation in which, as illustrated in FIG. 5(*b*), the adjustment can be more appropriately performed rather on the basis of the plurality of tomographic pictures obtained by scans that almost entirely cover the image capturing site. After completion of the second adjustment operation in the sequential display mode, the display mode switching button may be pressed to switch from the preliminary image capturing mode to the main image capturing mode in which, as illustrated in FIG. 5(*c*), 256 raster scans in total may be performed in the high-speed axis direction (x-direction) within the entire scanning region to capture tomographic images of the ocular fundus of the subject's eye E under the optimized image capturing condition. This flow may be the same as that of the first embodiment.

Figure 6:
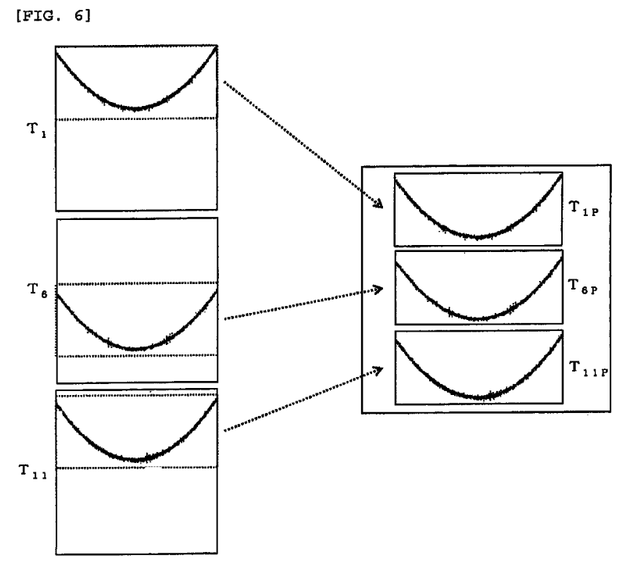
FIG. 6 is an explanatory view illustrating a modified example of displayed pictures in a selective display mode of the second embodiment.

In the present embodiment, the three tomographic pictures of tomographic picture $T_1$, tomographic picture $T_6$ and tomographic picture $T_{11}$ are displayed side by side in the same screen as they are, but the tomographic pictures may not necessarily be displayed as a whole in the screen. In an alternative embodiment, partial regions may be displayed which are selected so as to include the tomographic structure of the ocular fundus of the subject's eye to such an extent that is necessary for performing the first adjustment operation. For example, as illustrated in FIG. 6, for the selected plurality of tomographic pictures (three tomographic pictures of tomographic picture $T_1$, tomographic picture $T_6$ and tomographic picture $T_{11}$), only respective partial regions that include the tomographic structure of the ocular fundus of the subject's eye as the object may be enlarged, and the enlarged tomographic picture $T_{1P}$, tomographic picture $T_{6P}$ and tomographic picture $T_{11P}$ may be displayed side by side in the same screen.

When the selected plurality of tomographic pictures is displayed side by side in the same screen, the picture size of one tomographic picture to be displayed decreases as the number of the tomographic pictures increases and observation of details may be difficult. A part of tomographic picture that does not include the tomographic structure of the object is essentially unnecessary for the first adjustment operation. Therefore, as illustrated in FIG. 6, the part which does not include the tomographic structure of the object may be excluded from the displaying object, and only a region that includes the tomographic structure of the object necessary for the first adjustment operation may be enlarged thereby to allow for observation of details of the tomographic structure in each picture even when the plurality of tomographic pictures is displayed side by side in the same screen.

In an alternative embodiment, parts of the enlarged tomographic picture $T_{1P}$, tomographic picture $T_{6P}$ and tomographic picture $T_{11P}$ may be further enlarged and displayed side by side. This operation may be performed such that, when a region to be further enlarged is set within one tomographic picture (tomographic picture $T_{1P}$) of the plurality of enlarged tomographic pictures (tomographic picture $T_{1P}$, tomographic picture $T_{6P}$ and tomographic picture $T_{11P}$), corresponding regions at the same location are set as regions to be further enlarged in a coordinated manner also in other tomographic pictures (tomographic picture $T_{6P}$ and tomographic picture $T_{11P}$), or such that a region to be independently further enlarged is set for each of the plurality of enlarged tomographic pictures. When the regions are set in a cooperated manner in the plurality of enlarged tomographic pictures, the operation may be performed such that, when the region to be set in one tomographic picture is moved, corresponding regions are moved in a cooperated manner also in other tomographic pictures.

The tomographic image capturing device according to the present invention has been described hereinbefore with reference to the drawings, but the present invention is not limited to the above embodiments and various modified embodiments are possible.

DESCRIPTION OF REFERENCE NUMERALS

E Subject's eye (object)
10 Demultiplexing/multiplexing optical system
11 Low-coherence light source
12 Light power adjustment mechanism
13 Optical coupler
14 Collimator lens
20 Beam splitter
30 Measurement optical system
31 Focusing lens
34 X-axis scanning mirror
35 Y-axis scanning mirror
36 Scanning lens
37 Dichroic mirror
38 Objective lens
40 Reference optical system
42 Dispersion compensation glass for objective lens
46 Dichroic mirror
47 Focusing lens
48 Variable aperture
49 Reference mirror
50 Subject's eye dispersion compensation glass

The invention claimed is:

1. A tomographic image capturing device comprising a display means configured to:
split light from a light source into measurement light and reference light and cause the measurement light and the reference light to be incident to an object and a reference object, respectively;
capture tomographic images of the object on a basis of interference light generated by superposition of the measurement light reflected from the object and the reference light reflected from the reference object; and
display tomographic pictures of the object generated on a basis of the captured tomographic images,
the tomographic image capturing device having a first image capturing mode and a second image capturing mode,
the first image capturing mode being a mode in which the measurement light is two-dimensionally scanned by raster scan to be incident to the object and the tomographic images of the object are captured,
the second image capturing mode being a mode in which the measurement light is two-dimensionally scanned by raster scan to be incident to the object and the tomographic images of the object are captured, the raster scan in the second image capturing mode being thinned from the raster scan in the first image capturing mode,
the display means being configured to be switchable between a first display mode and a second display mode,
the first display mode being a mode in which a plurality of tomographic pictures including a region of interest of the object is selected from among the tomographic pictures generated on the basis of the tomographic images captured in the second image capturing mode and only the selected plurality of tomographic pictures is displayed,
the second display mode being a mode in which all of the tomographic pictures generated on the basis of the tomographic images captured in the second image capturing mode are in turn displayed,
the capturing of the tomographic images in the first image capturing mode being performed after separately performing a first adjustment operation and a second adjustment operation for adjustment of an image capturing condition necessary for capturing the tomographic images in the first image capturing mode, the first adjustment operation being based on the tomographic pictures displayed in the first display mode, the second adjustment operation being based on the tomographic pictures displayed in the second display mode.

2. The tomographic image capturing device as recited in claim 1, wherein, in the first display mode, the display means displays the selected plurality of tomographic pictures repetitively in turn.

3. The tomographic image capturing device as recited in claim 1, wherein, in the first display mode, the display means displays the selected plurality of tomographic pictures side by side in same screen.

4. The tomographic image capturing device as recited in claim 2 or 3, wherein only a desired selected region can be displayed for each of the selected plurality of tomographic pictures.

5. The tomographic image capturing device as recited in claim 3, wherein only a region including a tomographic structure of the object is enlarged for each of the selected plurality of tomographic pictures and the enlarged tomographic pictures are displayed side by side in same screen.

* * * * *